US011369504B2

(12) United States Patent
Kates et al.

(10) Patent No.: US 11,369,504 B2
(45) Date of Patent: Jun. 28, 2022

(54) HAND BRACE

(71) Applicant: Madeleine Kates, Williamsville, NY (US)

(72) Inventors: Madeleine Rose Kates, Williamsville, NY (US); Andrew Moquin, Clarence, NY (US)

(73) Assignee: Madeleine Kates, Williamsville, NY (US)

( * ) Notice: Subject to any disclaimer, the term of this patent is extended or adjusted under 35 U.S.C. 154(b) by 4 days.

(21) Appl. No.: 16/824,611

(22) Filed: Mar. 19, 2020

(65) Prior Publication Data

US 2021/0290419 A1 Sep. 23, 2021

(51) Int. Cl.
*A61F 5/01* (2006.01)

(52) U.S. Cl.
CPC ...... *A61F 5/013* (2013.01); *A61F 2005/0132* (2013.01)

(58) Field of Classification Search
CPC .... A61F 5/013; A61F 5/05866; A61F 5/0118; A61F 5/05875; A61F 5/01; A61F 2007/0036; A61F 2007/0038; A41D 13/081; A41D 13/087; A61H 1/0285; A63B 23/16; A63B 71/14
USPC .......................................................... 602/21
See application file for complete search history.

(56) References Cited

U.S. PATENT DOCUMENTS

| | | | | |
|---|---|---|---|---|
| 4,070,027 A | * | 1/1978 | Kifferstein | A63B 69/0059 473/214 |
| 4,854,310 A | * | 8/1989 | Lee | A61F 5/05866 602/21 |
| 5,409,451 A | * | 4/1995 | Daneman | A61F 5/05866 602/20 |
| 5,836,902 A | * | 11/1998 | Gray | A61F 5/0111 602/5 |
| 6,520,925 B1 | * | 2/2003 | Thibodo, Jr. | A61F 5/05875 128/880 |
| 6,613,006 B1 | * | 9/2003 | Asherman | A61F 13/04 602/20 |
| 10,932,940 B2 | * | 3/2021 | Karasahin | A61F 5/0102 |
| 2002/0002348 A1 | * | 1/2002 | Wiggins | A61F 5/0118 602/21 |
| 2005/0101898 A1 | * | 5/2005 | Cohen | A61F 5/0118 602/21 |
| 2011/0046530 A1 | * | 2/2011 | Gaylord | A61F 5/0118 602/21 |
| 2013/0150762 A1 | * | 6/2013 | Summit | A61F 5/05841 602/20 |

* cited by examiner

*Primary Examiner* — Keri J Nelson
*Assistant Examiner* — Kevin S Albers
(74) *Attorney, Agent, or Firm* — Hodgson Russ LLP (57) ABSTRACT

A brace for a person's hand has a cradle shaped to extend over the side of the hand in the area between a person's wrist crease and pinky-finger. The cradle may include two opposing curved sides, each side being joined to the other along a longitudinal edge. Opposite the longitudinal edge, each side has a distal edge. The distal edges may be spaced apart from each other by a distance that is approximately the thickness of a person's hand in the area extending from the person's wrist crease to the interstice between the pinky-finger and ring-finger. The cradle is shaped to extend over a side of the wearer's hand between a person's wrist crease and pinky-finger.

56 Claims, 9 Drawing Sheets

HAND BRACE

FIELD OF THE INVENTION

The present invention relates to hand braces used to provide support, especially support to those with a condition known as Ehlers-Danlos Syndrome Type 3, or for those in need of connective tissue support localized in the hand.

BACKGROUND OF THE INVENTION

Ehlers-Danlos Syndrome Type 3 is a connective tissue disorder. Among the issues arising from this disorder are that joints easily dislocate or sublux (partial dislocations). When Ehlers-Danlos affects the hand, one joint may be out of alignment, but other portions of the hand are not. In such a situation, the side of the hand between the wrist crease and pinky-finger may be dislocated or subluxed, but the thumb and fingers (when not restricted by a brace) have a full range of movement. This creates problems with many activities, including brushing hair, cooking, holding a book, writing, and typing. For example, when typing too long, the hand bones may sublux and dislocate, creating a limp and nearly useless hand. In addition, the hand may become lax from overuse, resulting in a loss of control, which can create additional problems and/or be unsafe.

When such subluxation and/or dislocation occurs, the hand becomes highly malleable, and when leaned against a stationary object, the bones and tissues of the hand somewhat mold to the shape of the stationary object. An outcome from this situation may be a loss of proper function (sometimes for days), as well as problems resulting from stress imposed on nerves. Such problems may include pain, fatigue, muscle tensing, loss of motor control, nerve pain extending beyond the hand and into the entire arm, or dislocations of the hand or finger bones.

Because Ehlers-Danlos Syndrome Type 3 is a complex and rare condition, many times it is ignored or overlooked by the manufacturers of braces. With respect to hands, currently available braces often lack proper fit, and more often do not properly brace the side and middle of the hand. Braces currently on the market often are designed for a stable-bodied patient, rather than an Ehlers patient. For example, ace bandages (being comprised of stretchy material) do not offer enough support for the "stretchy" hand of an Ehlers patient. And, hard shell braces can be too rigid or provide too much support, which inhibits movement, and sometimes such braces allow the wrong muscles to tense or engage, while others become overworked and limp. Such prior art braces often brace parts of the hand that do not need bracing.

Currently on the market are braces serving as wrist guards for rollerbladders. Such wrist guards feature a hard plastic shell that primarily stabilizes the wrist, but offers little or incorrect support for the hand and fingers. And, such a brace takes mobility away from most of the hand, which is not helpful to someone who lacks mobility in only one section of the hand. Other types of braces, such as those for fingers (vertical supports, trigger finger splints, entire hand braces, and wrist supports, and wraps) fail to provide support for the bones in the middle of the hand between the fingers and wrist crease, while allowing for mobility for the unaffected part of the hand that is not in need of bracing.

SUMMARY OF THE INVENTION

The invention may be embodied as a brace having a cradle. The cradle may have a first opposing curved side and a second opposing curved side. The curved sides may be a framework that includes a plurality of substantially parallel segments. When the brace has been installed on a person's hand, the substantially parallel segments extend in a direction that is substantially perpendicular to a general direction of the person's fingers when the hand is open and at rest. When the brace is placed on a wearer's hand, one of the curved sides may overlap an anterior portion of the wearer's hand, and the other curved side may overlap a posterior portion of the wearer's hand in the area of the hand that resides between the wrist crease and pinky-finger.

The first and second curved sides may be joined along or share a longitudinal edge, which may provide a substantially flat surface. Each curved side may have a distal edge, and the distal edges may be spaced apart from each other by a distance that is approximately the thickness of a person's hand in the area extending from the person's wrist crease to the interstice between the pinky-finger and ring-finger. The cradle may be shaped to extend over at least a portion of a side of a hand between a person's wrist crease and pinky-finger. When positioned on the wearer's hand, the brace may substantially cover the portion of the wearer's hand that resides between the wrist crease and pinky-finger, including the side of the hand residing between the wearer's wrist crease and pinky-finger.

Some embodiments of the invention may include a pinky-finger ring attached to the cradle. The pinky-finger ring may be sized to surround a wearer's pinky-finger. The pinky-finger ring may extend from a longitudinal edge of the cradle that connects the curved sides to each other. The pinky-finger ring may extend from one of the curved sides.

Some embodiments of the brace may include at least one protrusion extending from the cradle near the distal edge in a direction that will grasp a wearer's hand when the cradle is installed on the wearer's hand. In this manner, the brace may hold to and overlap a portion of the wearer's hand in the area of the hand that resides between the wrist crease and pinky-finger.

BRIEF DESCRIPTION OF THE DRAWINGS

For a fuller understanding of the nature and objects of the invention, reference should be made to the accompanying drawings and the subsequent description. Briefly, the drawings are.

FURTHER DESCRIPTION OF THE INVENTION

The invention may be embodied as a brace 10 for a person's hand 13. The brace 10 may be useful for individuals having Ehlers-Danlos Syndrome Type 3, and it may be useful for people with arthritis, or other conditions.

Figure 12:
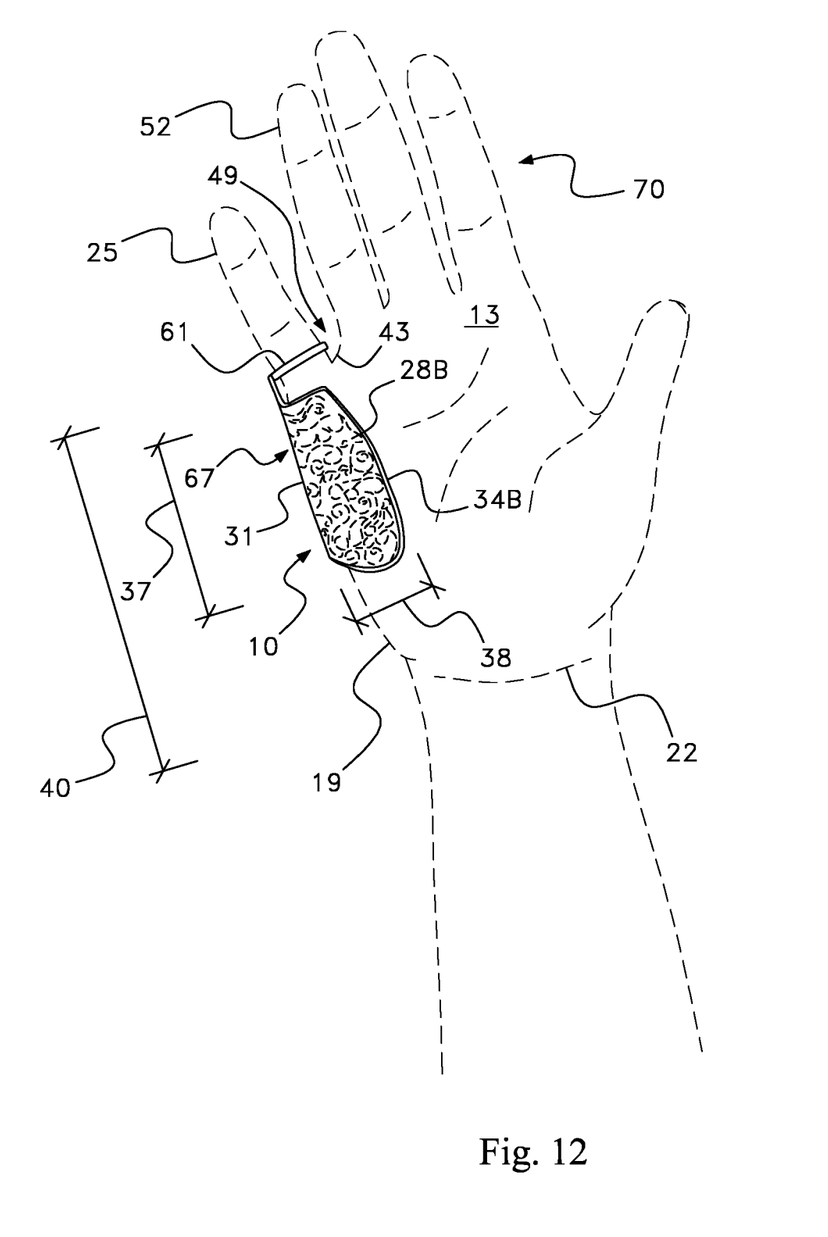
FIG. 12 depicts an embodiment of the brace having a decorative cradle.

FIGS. 1-11 depict an embodiment of the invention. FIG. 12 depicts a different embodiment of the invention. These embodiments of the invention have a brace 10 that includes a cradle 16 shaped to extend over the side 19 of the hand 13 in the area between a person's wrist crease 22 and pinky-finger 25. The cradle 16 may include two opposing curved sides 28A, 28B each side 28A, 28B being connected along a longitudinal edge 31. Opposite the longitudinal edge 31, each side has a distal edge 34A, 34B.

The cradle 16 may be sized and shaped to fit a particular person's hand 13. For example,
(a) the sides 28A, 28B may have a length 37 that is less than or equal to the distance 40 from the wearer's wrist crease 22 to the base 43 of the pinky-finger 25; and
(b) the distal edges 34A, 34B may be spaced apart from each other by a distance 46 that is approximately the thickness of a person's hand 13 in the area extending from the person's wrist crease 22 to the interstice 49 between the pinky-finger 25 and ring-finger 52.

The length 37 and width 38 of the curved sides 28A, 28B may be sized to cover a substantial portion of the wearer's hand 13 that is between the wrist crease 22 and pinky-finger 25. In this manner, when positioned on the wearer's hand 13, the brace 10 substantially covers that portion of the hand 13 that resides between the wrist crease 22 and pinky-finger 25, which includes the side 19 of the hand 13 residing between the wearer's wrist crease 22 and pinky-finger 25 and areas 55A, 55B of the hand 13 that are immediately adjacent to the side 19, which are sometimes referred to herein as the immediately adjacent anterior area 55A and the immediately adjacent posterior area 55B.

The cradle 16 may be a solid piece or a framework providing, in effect, an exoskeleton for the areas 55A, 55B (anterior and posterior) of the hand 13 that reside between the wrist crease 22 and pinky-finger 25 and immediately adjacent to the side 19. When placed over the areas 55A, 55B, the cradle 16 provides a rigid or nearly-rigid covering that limits movement of the hand bones, but allows movement of the pinky-finger 25 and wrist crease 22. Importantly, when the wearer rests her hand 13 on a surface 58, such as a desk, the cradle 16 distributes the force across the cradle 16. As the wearer moves her hand 13 (still resting on the surface 58), such as while writing, the cradle 16 not only distributes the force, but also limits the manner in which the hand bones are permitted to move, thereby keeping the hand bones close to their natural (and desired) relative positions.

The brace 10 may include a ring 61 through which the pinky-finger 25 extends. Such a ring 61 helps to keep the cradle properly 16 positioned on the hand 13. FIGS. 1 through 11 depict a framework-version of the cradle 16 with an integral pinky-receiving ring 61. FIG. 12 depicts a different version of the cradle 16 that has a decorative exterior-facing side. Such a decorative exterior may constitute or augment the curved sides 28A and/or 28B.

The cradle 16 (and pinky-receiving ring 61 if included) may be made from many types of materials, including many metals and plastics. A good choice of material may have the following characteristics:

(a) at about room-temperature, the material will be suitably rigid while also being somewhat resilient, and thus provide adequate support and also the ability to flex a small amount without permanent deformation, and return to its original shape after small forces are applied, such as those forces needed to place the brace 10 on the hand 13, or remove the brace 10 from the hand;

(b) at temperatures slightly above those in which humans can commonly be found, the material will be somewhat malleable to permit some size and shape adjustment;

(c) the material will be washable using mild cleaners commonly found in households; and (d) the material will be hypo-allergenic.

A material that exhibits these desired characteristics is 14 k rose gold. Metals such as stainless steel or tungsten may not be ideal because they become malleable only at temperatures well above temperatures in which humans can commonly be found, and thus do not easily accommodate adjustment for shape and therefore it may be difficult to achieve proper fit of the brace 10 to a specific individual's preference. Other metals, such as platinum, are too heavy and/or very expensive. Still others, such as white gold, may have impurities that some wearers may be allergic to. Finally, metals such as yellow gold are not highly resilient at room temperature and may change shape over time, especially if subjected to forces and/or heat, and are easily scratched or worn away.

The material and thickness of the cradle 16 may be selected to provide a desired flexibility, in order to suit the wearer's needs and desires. For example, the flexibility of the cradle 16 may be selected so that the cradle 16 is slightly deformed with a small force to increase the distance between the distal edges 34A, 34B as the areas 55A, 55B of the hand 13 area are placed within the cradle 16. In this manner, the cradle 16 forms a friction-fit with the wearer's hand 13, and thereby grasps the wearer's hand 13. Those versions of the brace 10 that do not include a pinky-receiving ring 61 may be formed and fitted to provide more grasping force than other versions of the brace 10.

Figure 1:
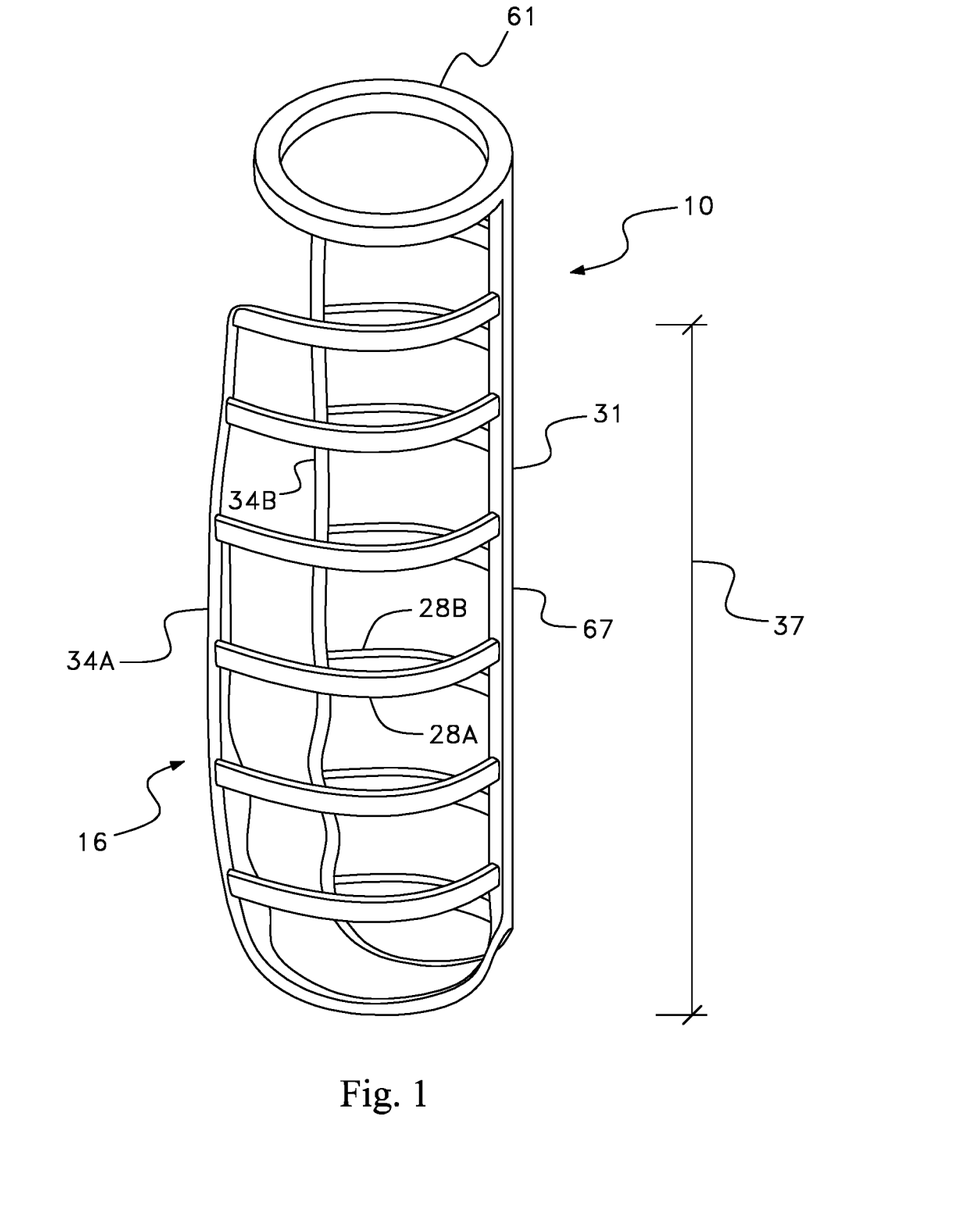
FIG. 1, which is a perspective view of a brace according to the invention.
Figures 2, 3:
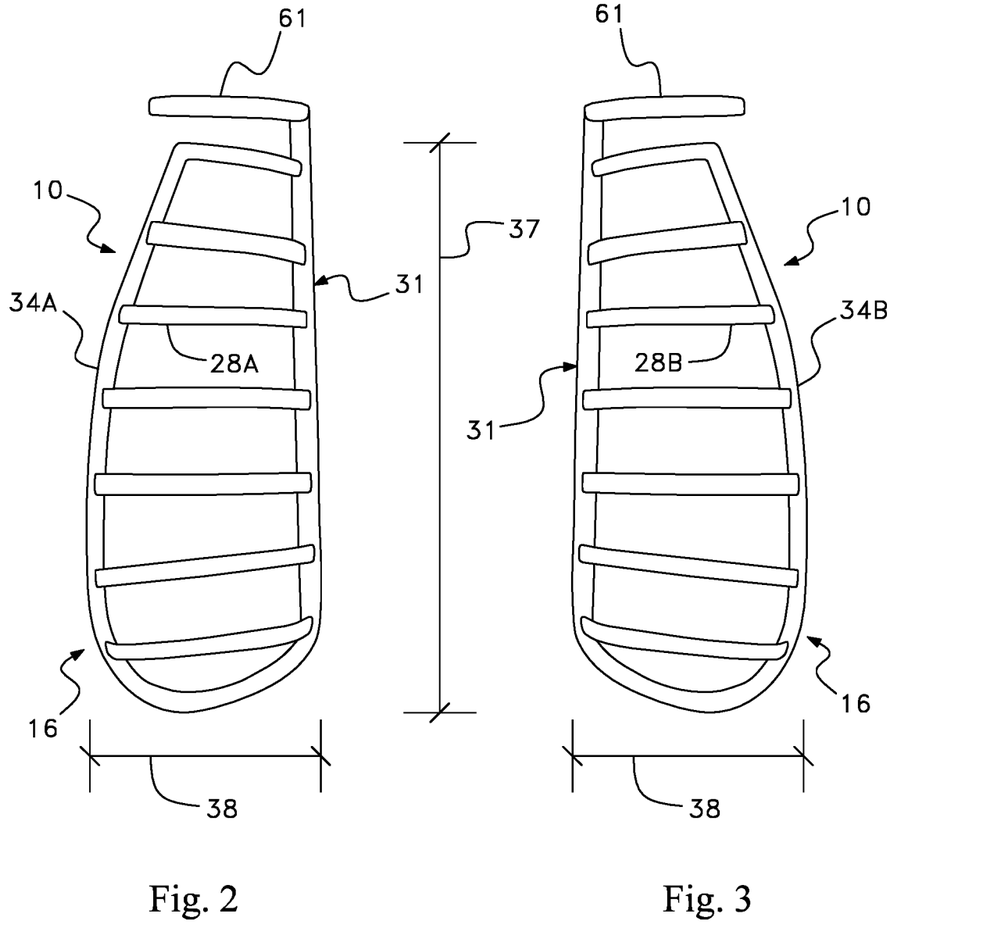
FIG. 2, which is a side view of the brace shown in FIG. 1.
FIG. 3, which is another side view of the brace shown in FIG. 1.
Figures 4, 5:
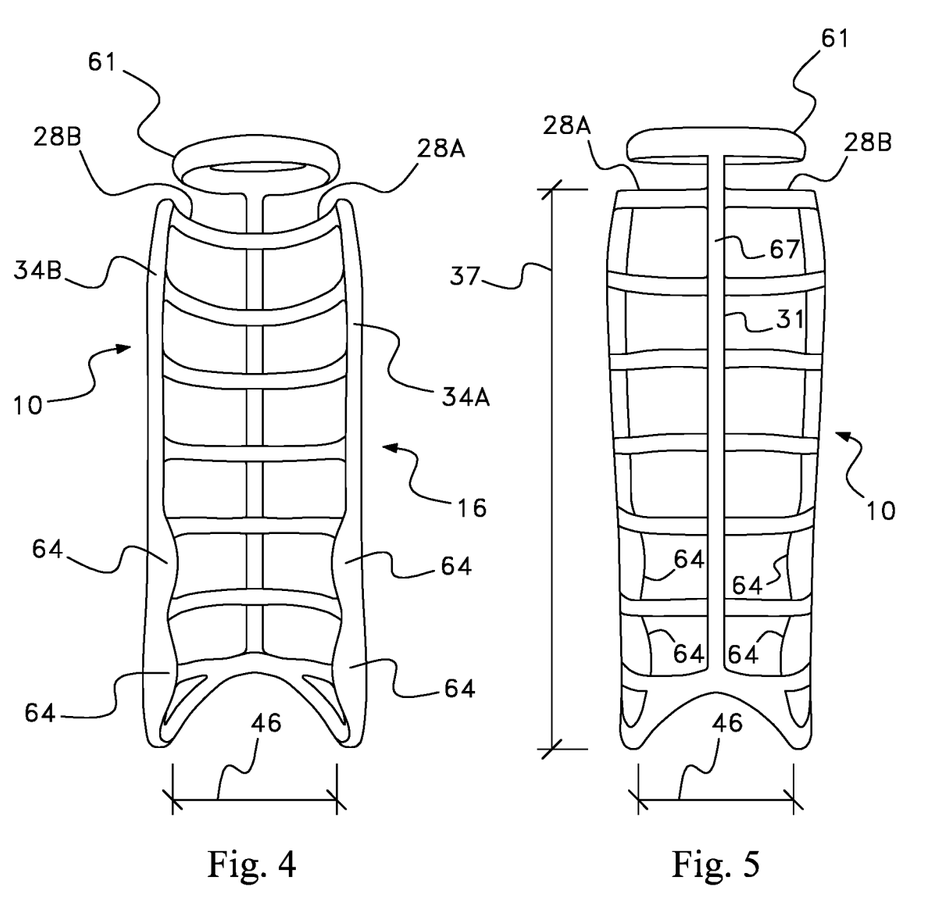
FIG. 4, which is another perspective view of the brace shown in FIG. 1.
FIG. 5, which is a different perspective view of the brace shown in FIG. 1.
Figure 6:
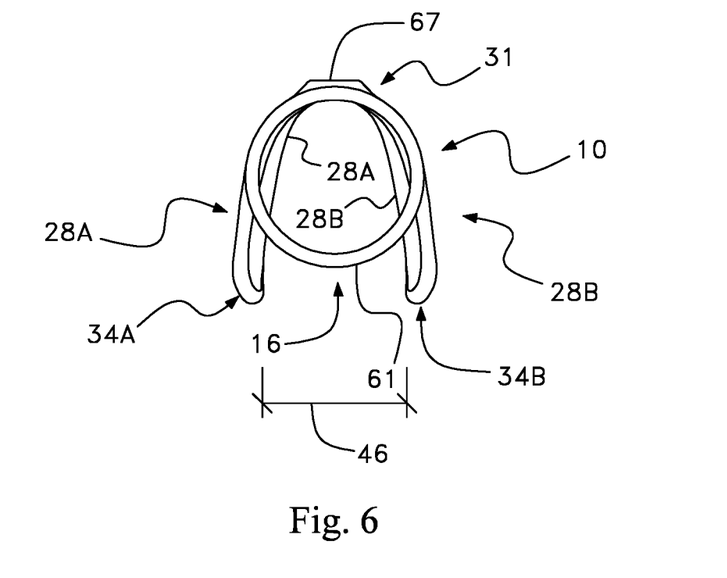
FIG. 6, which is an end view of the brace shown in FIG. 1.
Figure 7:
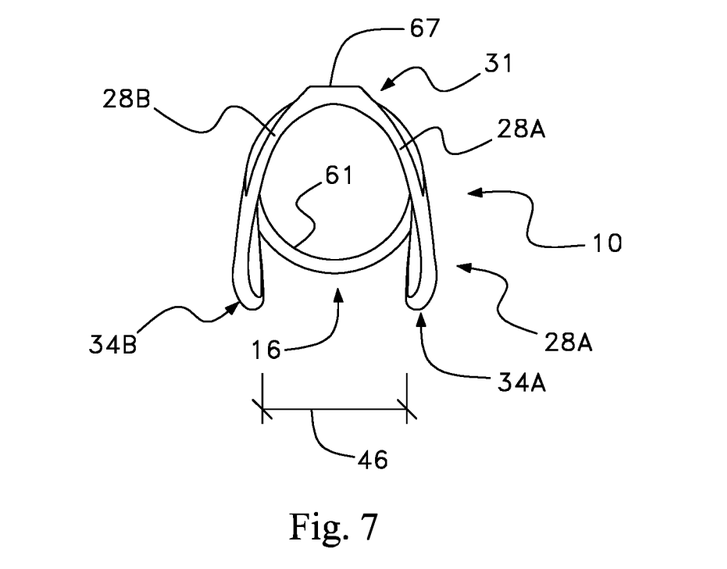
FIG. 7, which is another end view of a brace according to the invention.
Figure 8:
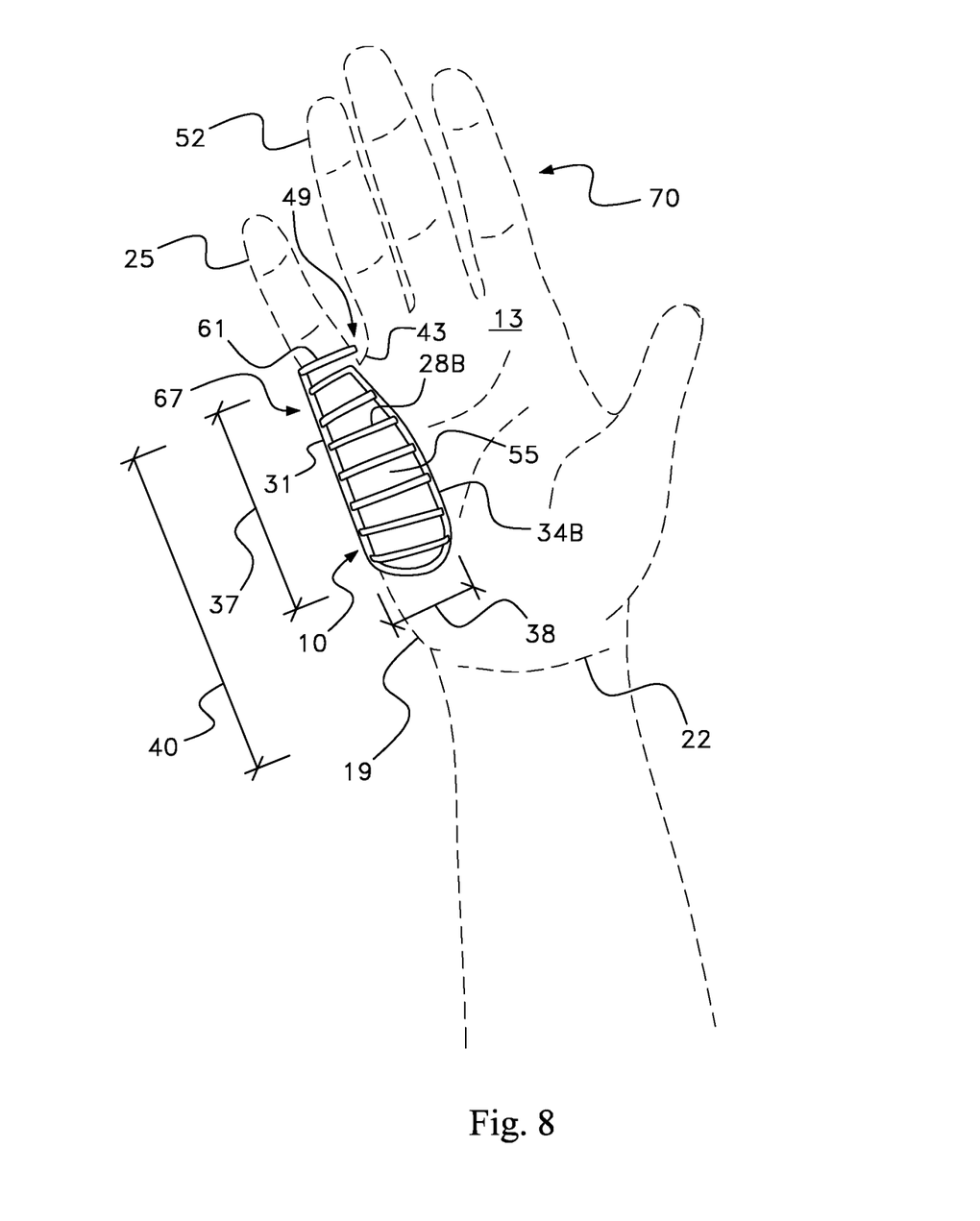
FIG. 8, which is a side view of a brace according to the invention shown mounted on a wearer's hand and viewed from the anterior side.
Figure 9:
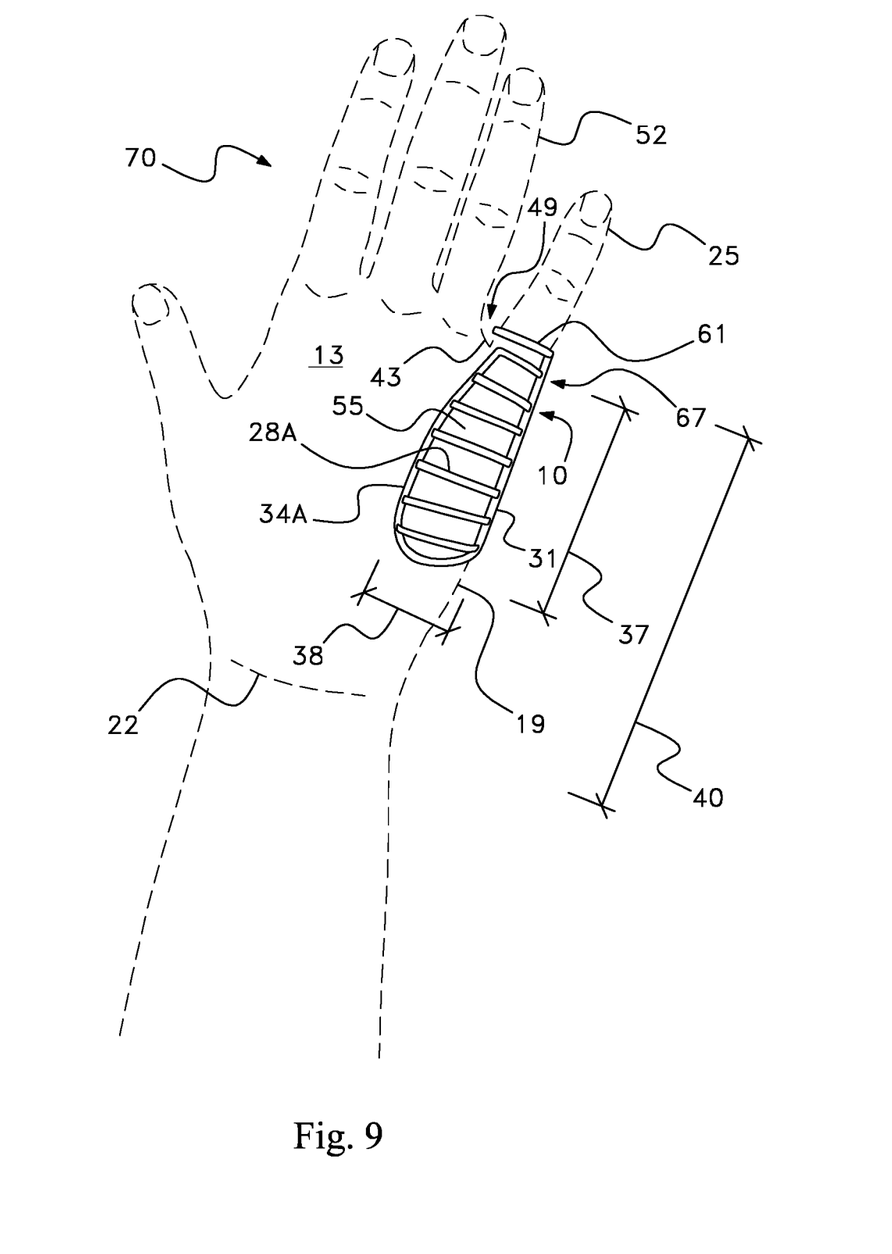
FIG. 9, which is a side view of the brace shown in FIG. 8 viewed from the posterior side.
Figure 10:
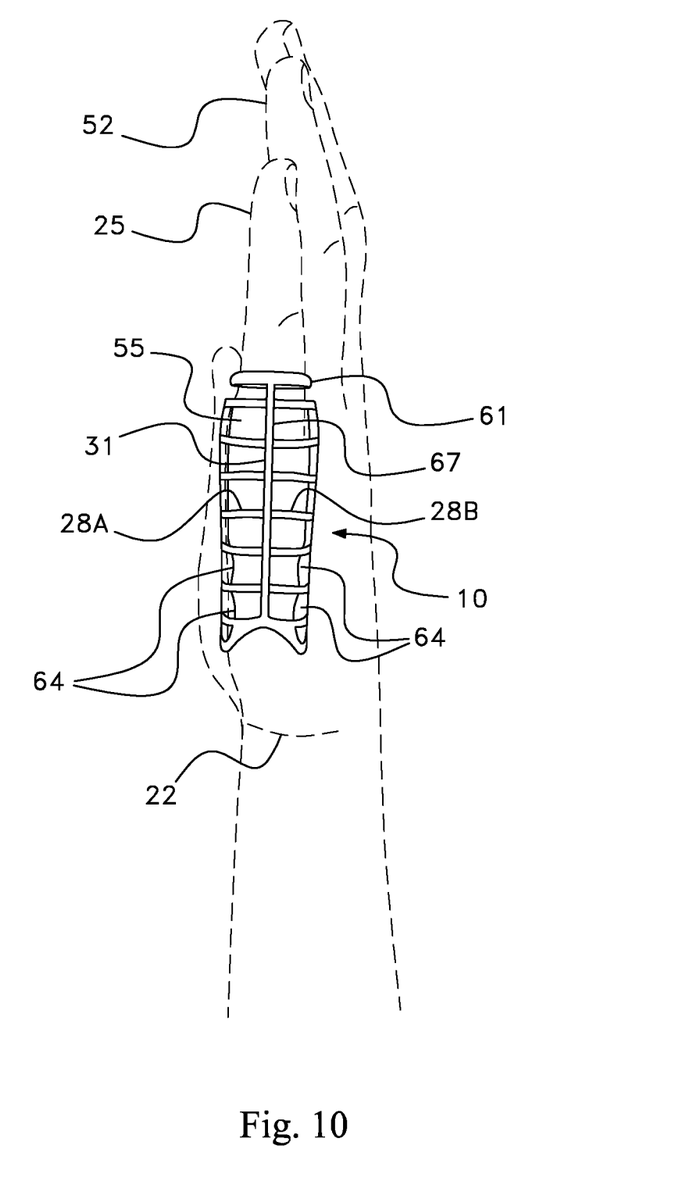
FIG. 10, which is a side view of the brace shown in FIG. 8.
Figure 11:
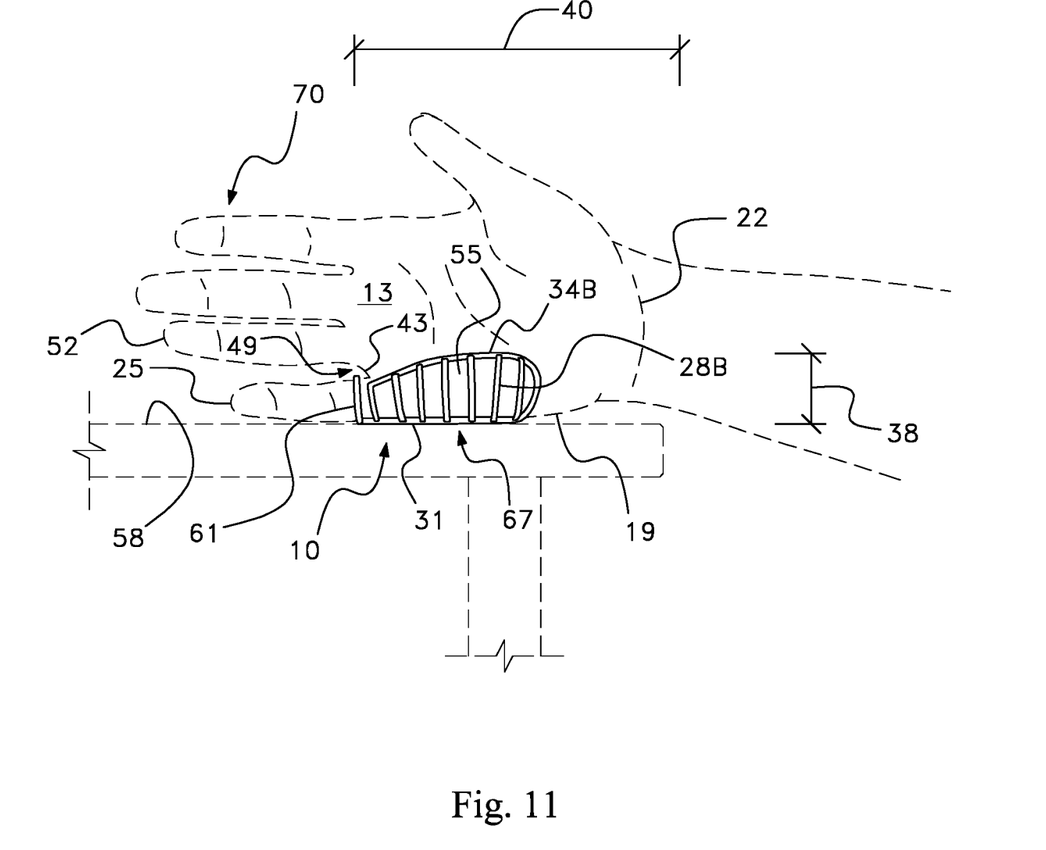
FIG. 11, which is another side view of the brace shown in FIG. 8.

FIGS. 4, 5, and 10 depict four protrusions residing at the distal edges 34A, 34B of the cradle 16 near a wrist-end of the cradle 16. These protrusions 64 grasp the wearer's hand 13 in order to help hold the cradle 16 on the hand 13. The protrusions 64 shown in FIGS. 4, 5, and 10 are in the form of arcs in order to avoid sharp edges that might damage the skin of the person wearing the brace 10.

The longitudinal edge 31 of the cradle 16 may include a relatively flat surface 67 residing roughly in the middle of the cradle 16 between the opposing curved sides 28A, 28B, and extending (when the brace 10 is on the hand 13) lengthwise along the side 19. Such a relatively flat surface 67 allows the wearer to rest the cradle 16 on another surface 58, such as a table, and the wearer can then use the surface 67 to provide support while also permitting the cradle 16 to easily glide along the table surface 58, which may be useful for facilitating writing.

Braces 10 according to the invention may serve to keep the hand bones near the side 19 in proper position, and may also serve to guide mis-positioned hand bones into proper position. Such braces 10 may be especially useful when reading, typing, or writing because the hand 13 is supported but the fingers 70 are available to turn pages, push keys, or hold writing instruments (e.g. pens and pencils). In addition, the wearer's wrist crease 22 is free to move in order to place the wearer's fingers 70 in a desired position. Furthermore, such a brace 10 may be found to have therapeutic applications when wearing the brace 10 after one of these activities to then reshape the hand 13 into its proper position more quickly.

Now that features of the invention and some embodiments of the invention have been described, Statements (non-limiting) of various embodiments of the invention are as follows:

Statement A: A hand brace, comprising a cradle having a first opposing curved side, a second opposing curved side, and a longitudinal edge, wherein:
  (a) the first and second curved sides extend from the longitudinal edge;
  (b) each curved side has a distal edge, the distal edges being spaced apart from each other by a distance that is approximately the thickness of a person's hand in an area extending from the person's wrist crease to an interstice between a pinky-finger of the person's hand and a ring-finger of the person's hand; and
  (c) the cradle is shaped to extend over an edge of the person's hand between the person's wrist crease and the pinky-finger.

Statement B: The hand brace of Statement A, wherein the longitudinal edge is positioned relative to the curved sides so that when the brace is on the person's hand the longitudinal edge extends along the edge of the person's hand between the wrist crease and the pinky finger.

Statement C: The hand brace of Statement A or Statement B, further comprising a pinky-finger ring attached to the cradle, the pinky-finger ring being sized to surround the pinky-finger.

Statement D: The hand brace of Statement C, wherein the pinky-finger ring is attached to one of the curved sides.

Statement E: The hand brace of Statement C, wherein the pinky-finger ring is attached to the longitudinal edge.

Statement F: The hand brace of any of the foregoing Statements, wherein the cradle comprises a framework.

Statement G: The hand brace of Statement F, wherein the framework includes a plurality of substantially parallel segments, wherein the substantially parallel segments are oriented such that when the brace is on the person's hand, the substantially parallel segments extend in a direction that is substantially perpendicular to a general direction of the person's fingers when the hand is open and the fingers are side-by-side.

Statement H: The hand brace of Statement F, wherein the framework includes a plurality of substantially parallel segments extending from the longitudinal edge.

Statement H': The hand brace of Statement G, wherein the substantially parallel segments extending from the longitudinal edge.

Statement I: The hand brace of Statement F, wherein the framework includes the curved sides, and each of the curved sides includes a plurality of substantially parallel segments.

Statement J: The hand brace of Statement I, wherein each of the substantially parallel segments extends from the longitudinal edge.

Statement K: The hand brace of any one of the foregoing Statements, wherein the curved sides are oriented relative to the longitudinal edge such that when the brace is placed on the person's hand, one of the curved sides overlaps an anterior portion of the person's hand, and the other curved side overlaps a posterior portion of the person's hand, the anterior portion and posterior portion including an area of the person's hand that resides between the person's wrist crease and pinky-finger.

Statement L: The hand brace of any one of the foregoing Statements, further comprising at least one protrusion extending from the cradle in a direction so that the at least one protrusion will grasp the person's hand when the brace is on the person's hand.

Statement M: The hand brace of Statement L, wherein the at least one protrusion extends from the cradle at substantially 90 degrees.

Statement N: The hand brace of any one of the foregoing Statements A through K, further comprising a first protrusion extending from the first curved side, and a second protrusion extending from the second curved side, each protrusion extending in a direction that is toward the person's hand when the brace is on the person's hand.

Statement O: The hand brace of Statement N, wherein the first protrusion extends toward the second curved side.

Statement O': The hand brace of Statement N, wherein the first protrusion extends at substantially 90 degrees from the first curved side.

Statement P: The hand brace of Statement O or Statement O', wherein the second protrusion extends toward the first curved side.

Statement P': The hand brace of Statement O or Statement O', wherein the second protrusion extends at substantially 90 degrees from the first curved side.

Statement Q: The hand brace of Statement N, wherein at least one of the protrusions extends from the cradle at substantially 90 degrees.

Statement R: The hand brace of any one of the foregoing Statements, wherein the longitudinal edge includes a substantially flat longitudinal surface extending along the longitudinal edge.

Statement S: The hand brace of Statement R, wherein the substantially flat longitudinal surface faces in a direction that is, when the brace is on the person's hand, away from the edge of the person's hand between the person's wrist crease and the pinky-finger.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:
1. A hand brace, comprising a cradle having a first opposing curved bar, a second opposing curved bar, and a rigid longitudinal bar, wherein:
  (a) the first and second curved bars extend from the longitudinal bar;
  (b) each curved bar has a distal edge spaced apart from the longitudinal bar, the distal edges being configured and spaced apart from each other by a distance that is approximately a thickness of a person's hand in an area enveloped by the cradle between the person's wrist crease and an interstice between a pinky-finger of the person's hand and a ring-finger of the person's hand; and
  (c) the cradle is shaped and configured to extend over the person's hand between the person's wrist crease and the pinky-finger;
  (d) wherein the longitudinal bar:
    (i) has a substantially flat, externally-facing surface extending lengthwise along the longitudinal bar; and

(ii) is positioned relative to the curved bars so that when the cradle is on the person's hand, the longitudinal bar is configured to extend along the edge of the person's hand between the person's wrist crease and the pinky finger; and (e) the cradle is shaped and configured to allow free movement of the wrist when the cradle is installed on the person's hand.

2. The hand brace of claim 1, further comprising a pinky-finger ring attached to the cradle, the pinky-finger ring being positioned and configured to surround the pinky-finger of the person's hand.

3. The hand brace of claim 2, wherein the pinky-finger ring is attached to one of the curved bars.

4. The hand brace of claim 2, wherein the pinky-finger ring is attached to the longitudinal bar.

5. The hand brace of claim 1, wherein the cradle comprises a framework.

6. The hand brace of claim 5, wherein the framework includes at least three substantially parallel segments directly connected to the longitudinal bar, wherein the substantially parallel segments are oriented such that when the cradle is on the person's hand, the substantially parallel segments extend in a direction that is substantially perpendicular to a general direction of the person's fingers when the hand is open and the fingers are side-by-side.

7. The hand brace of claim 5, wherein the framework includes at least three substantially parallel segments extending from the longitudinal bar.

8. The hand brace of claim 5, wherein the framework includes at least three substantially parallel segments.

9. The hand brace of claim 8, wherein each of the substantially parallel segments extends from the longitudinal bar to one of the curved bars.

10. The hand brace of claim 1, wherein the curved bars are oriented relative to the longitudinal bar such that when the cradle is installed on the person's hand, one of the curved bars overlaps an anterior portion of the person's hand, and the other curved bar overlaps a posterior portion of the person's hand, the anterior portion and posterior portion including an area of the person's hand that resides between the person's wrist crease and pinky-finger.

11. The hand brace of claim 1, further comprising at least one protrusion extending from the cradle in a direction so that the at least one protrusion will grasp the person's hand when the cradle is installed on the person's hand.

12. The hand brace of claim 11, wherein the at least one protrusion extends from the cradle at substantially 90 degrees.

13. The hand brace of claim 1, further comprising a first protrusion extending from the first curved bar, and a second protrusion extending from the second curved bar, each protrusion extending in a direction that is toward the person's hand when the cradle is installed on the person's hand.

14. The hand brace of claim 1, further comprising a first protrusion extending from the first curved bar, and a second protrusion extending from the second curved bar, wherein the first protrusion extends toward the second curved bar.

15. The hand brace of claim 14, wherein the second protrusion extends toward the first curved bar.

16. The hand brace of claim 13, wherein at least one of the protrusions extends from the cradle at substantially 90 degrees.

17. The hand brace of claim 1, wherein the externally-facing surface faces in a direction that is, when the cradle is installed on the person's hand, away from the edge of the person's hand between the person's wrist crease and the pinky-finger.

18. A hand brace, comprising a cradle having a first opposing curved bar, a second opposing curved bar, and a rigid longitudinal bar, wherein:

(a) the first and second curved sidebars extend from the longitudinal bar;

(b) each curved bar has a distal edge spaced apart from the longitudinal bar, the distal edges being configured and spaced apart from each other by a distance that is approximately the thickness of a person's hand in an area enveloped by the cradle between the person's wrist crease and an interstice between a pinky-finger of the person's hand and a ring-finger of the person's hand; and (c) the cradle is shaped and configured to extend over the person's hand between the person's wrist crease and the pinky-finger; and the cradle is shaped and configured to allow free movement of the wrist when the cradle is installed on the person's hand; and the hand brace further comprises a pinky-finger ring attached to one of the curved bars or the longitudinal bar, the pinky-finger ring being positioned and configured to surround the pinky-finger of the person's hand.

19. The hand brace of claim 18, wherein the longitudinal bar is positioned relative to the curved bars so that when the cradle is installed on the person's hand the longitudinal bar extends along the edge of the person's hand between the wrist crease and the pinky finger.

20. The hand brace of claim 18, wherein the pinky-finger ring extends from the longitudinal bar and is spaced apart from the cradle.

21. The hand brace of claim 18, wherein the cradle comprises a framework.

22. The hand brace of claim 21, wherein the framework includes at least three substantially parallel segments directly connected to the longitudinal bar, wherein the substantially parallel segments are oriented such that when the cradle is installed on the person's hand, the substantially parallel segments extend in a direction that is substantially perpendicular to a general direction of the person's fingers when the hand is open and the fingers are side-by-side.

23. The hand brace of claim 21, wherein the framework includes at least three of substantially parallel segments extending from the longitudinal bar.

24. The hand brace of claim 21, wherein the framework includes at least three of substantially parallel segments.

25. The hand brace of claim 24, wherein each of the substantially parallel segments extends from the longitudinal bar to one of the curved bars.

26. The hand brace of claim 18, wherein the curved bars are oriented relative to the longitudinal bar such that when the cradle is installed on the person's hand, one of the curved bars overlaps an anterior portion of the person's hand, and the other curved bar overlaps a posterior portion of the person's hand, the anterior portion and posterior portion including an area of the person's hand that resides between the person's wrist crease and pinky-finger.

27. The hand brace of claim 18, further comprising at least one protrusion extending from the cradle in a direction so that the at least one protrusion will grasp the person's hand when the cradle is installed on the person's hand.

28. The hand brace of claim 27, wherein the at least one protrusion extends from the cradle at substantially 90 degrees.

29. The hand brace of claim 18, further comprising a first protrusion extending from the first curved bar, and a second protrusion extending from the second curved bar, each protrusion extending in a direction that is toward the person's hand when the cradle is installed on the person's hand.

30. The hand brace of claim 18, further comprising a first protrusion extending from the first curved bar, and a second protrusion extending from the second curved bar wherein the first protrusion extends toward the second curved bar.

31. The hand brace of claim 30, wherein the second protrusion extends toward the first curved bar.

32. The hand brace of claim 29, wherein at least one of the protrusions extends from the cradle at substantially 90 degrees.

33. The hand brace of claim 18, wherein the longitudinal bar includes a substantially flat, externally facing surface extending lengthwise along the longitudinal bar.

34. The hand brace of claim 18, wherein the externally facing surface faces in a direction that is, when the cradle is installed on the person's hand, away from the edge of the person's hand between the person's wrist crease and the pinky-finger.

35. A hand brace, comprising a cradle having a first opposing curved bar, a second opposing curved bar, and a rigid longitudinal bar, wherein:
(a) the first and second curved bar extend from the longitudinal bar;
(b) each curved bar has a distal edge spaced apart from the longitudinal bar, the distal edges being configured and spaced apart from each other by a distance that is approximately a thickness of a person's hand in an area enveloped by the cradle between the person's wrist crease and an interstice between a pinky-finger of the person's hand and a ring-finger of the person's hand; and
(c) the cradle is shaped and configured to extend over the person's hand between the person's wrist crease and the pinky-finger; and
(d) the cradle includes a framework and the framework includes at least three substantially parallel segments extending between the longitudinal bar and one of the curved bars; and
(e) the hand cradle is shaped and configured to allow free movement of the wrist when the cradle is installed on the person's hand.

36. The hand brace of claim 35, wherein the longitudinal bar is positioned relative to the curved bars so that when the cradle is installed on the person's hand the longitudinal bar extends along the edge of the person's hand between the wrist crease and the pinky finger.

37. The hand brace of claim 35, further comprising a pinky-finger ring attached to the cradle, the pinky-finger ring being positioned and configured to surround the pinky-finger of the person's hand.

38. The hand brace of claim 37, wherein the pinky-finger ring is attached to one of the curved bars.

39. The hand brace of claim 37, wherein the pinky-finger ring is attached to the longitudinal bar.

40. The hand brace of claim 35, wherein the substantially parallel segments are directly connected to the longitudinal bar.

41. The hand brace of claim 35, wherein the substantially parallel segments are oriented such that when the cradle is installed on the person's hand, the substantially parallel segments extend in a direction that is substantially perpendicular to a general direction of the person's fingers when the hand is open and the fingers are side-by-side.

42. The hand brace of claim 35, wherein the at least three substantially parallel segments extending from the longitudinal bar.

43. The hand brace of claim 35, wherein the substantially parallel segments extend from one of the curved bars.

44. The hand brace of claim 35, wherein each of the substantially parallel segments extends from the longitudinal bar to one of the curved bars.

45. The hand brace of claim 35, wherein the curved bars are oriented relative to the longitudinal bar such that when the cradle is installed on the person's hand, one of the curved bars overlaps an anterior portion of the person's hand, and the other curved bar overlaps a posterior portion of the person's hand, the anterior portion and posterior portion including an area of the person's hand that resides between the person's wrist crease and pinky-finger.

46. The hand brace of claim 35, further comprising at least one protrusion extending from the cradle in a direction so that the at least one protrusion will grasp the person's hand when the brace is installed on the person's hand.

47. The hand brace of claim 46, wherein the at least one protrusion extends from the cradle at substantially 90 degrees.

48. The hand brace of claim 35, further comprising a first protrusion extending from the first curved bar, and a second protrusion extending from the second curved bar, each protrusion extending in a direction that is toward the person's hand when the cradle is installed on the person's hand.

49. The hand brace of claim 35, further comprising a first protrusion extending from the first curved bar, and a second protrusion extending from the second curved bar, wherein the first protrusion extends toward the second curved-bar.

50. The hand brace of claim 49, wherein the second protrusion extends toward the first curved bar.

51. The hand brace of claim 48, wherein at least one of the protrusions extends from the cradle at substantially 90 degrees.

52. The hand brace of claim 35, wherein the longitudinal bar includes a substantially flat longitudinal surface extending lengthwise along the longitudinal bar.

53. The hand brace of claim 52, wherein the substantially flat longitudinal surface faces in a direction that is, when the cradle is installed on the person's hand, away from the person's hand between the person's wrist crease and the pinky-finger.

54. The hand brace of claim 1, wherein the longitudinal bar is substantially straight.

55. The hand brace of claim 18, wherein the longitudinal bar is substantially straight.

56. The hand brace of claim 35, wherein the longitudinal bar is substantially straight.

\* \* \* \* \*